(12) United States Patent
Masood et al.

(10) Patent No.: US 8,958,618 B2
(45) Date of Patent: Feb. 17, 2015

(54) METHOD AND SYSTEM FOR IDENTIFICATION OF CALCIFICATION IN IMAGED BLOOD VESSELS

(75) Inventors: Saad Masood, Edinburgh (GB); Brian Mohr, Edinburgh (GB); Costas Plakas, Edinburgh (GB)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 307 days.

(21) Appl. No.: 13/535,895

(22) Filed: Jun. 28, 2012

(65) Prior Publication Data

US 2014/0003701 A1 Jan. 2, 2014

(51) Int. Cl.
G06K 9/00 (2006.01)
G06K 9/34 (2006.01)
G06K 9/62 (2006.01)

(52) U.S. Cl.
USPC ........... 382/131; 382/134; 382/154; 382/173; 382/225

(58) Field of Classification Search
USPC ................. 382/131, 154, 173, 225
See application file for complete search history.

(56) References Cited

U.S. PATENT DOCUMENTS

| | | | |
|---|---|---|---|
| 6,751,354 B2 * | 6/2004 | Foote et al. | 382/224 |
| 7,593,562 B2 * | 9/2009 | Harrington et al. | 382/141 |
| 2006/0173663 A1 * | 8/2006 | Langheier et al. | 703/11 |
| 2007/0165921 A1 * | 7/2007 | Agam et al. | 382/128 |

OTHER PUBLICATIONS

Lei, T.; Sewchand, W., "Statistical approach to X-ray CT imaging and its applications in image analysis. I. Statistical analysis of X-ray CT imaging," Medical Imaging, IEEE Transactions on, vol. 11, No. 1, pp. 53,61, Mar. 1992.*
Yin Wang; Liatsis, P., "A Fully Automated Framework for Segmentation and Stenosis Quantification of Coronary Arteries in 3D CTA Imaging," Developments in eSystems Engineering (DESE), 2009 Second International Conference on, vol., no., pp. 136,140, Dec. 14-16, 2009.*
Arash Taki, Zahra Najafi, Alireza Roodaki, S. K. Setarehdan, R. A. Zoroofi, Andreas Konig, Nassir Navab, "Automatic segmentation of calcified plaques and vessel borders in IVUS images" International Journal of Computer Assisted Radiology and Surgery, Sep. 2008, vol. 3, Issue 3-4, pp. 347-354.*

(Continued)

Primary Examiner — Utpal Shah
(74) Attorney, Agent, or Firm — Oblon, Spivak, McClelland, Maier & Neustadt, L.L.P.

(57) ABSTRACT

A computer implemented method identifying calcification in a patient image data set including blood vessels. The method includes: obtaining an image data set including voxels each having an intensity value; forming the intensity values into an intensity value group covering an intensity range; defining plural intensity thresholds across the intensity range and including its end values; for each intensity threshold, partitioning the intensity values into two sub-groups according to intensity threshold, and calculating an information criterion based on intensity threshold; generating an information criterion measure curve that plots the calculated information criteria against intensity threshold; locating a maximum in the information criterion measure curve and setting the corresponding intensity threshold as a calcification threshold; and partitioning the intensity values into two sub-groups using the calcification threshold, identifying voxels corresponding to intensity values in the sub-group above the calcification threshold as representing calcification in the patient.

48 Claims, 12 Drawing Sheets

(56) References Cited

OTHER PUBLICATIONS

Zhang, J.; Modestino, J., "A model-fitting approach to cluster validation with application to stochastic model-based image segmentation," Pattern Analysis and Machine Intelligence, IEEE Transactions on, vol. 12, No. 10, pp. 1009,1017, Oct. 1990.*

Qinpei Zhao et al., "Knee Point Detection in BIC for Detecting the Number of Clusters", Advanced Concepts for Intelligent Vision Systems, vol. 5259, 2008, pp. 664-673.

J. MacQueen, "Some Methods for Classification and Analysis of Multivariate Observations", Proceedings of the 5$^{th}$ Symposium of Math, Statistics, and Probability, University of California Press, 1967, pp. 281-297.

Jose L. Marroquin et al., "Some Extensions of the K-Means Algorithm for Image Segmentation and Pattern Classification", AI Memo 1390, Massachusetts Institute of Technology, Cambridge, MA, 1993, 16 Pages.

Todd K. Moon, "The Expectations-Maximization Algorithm", Signal Processing Magazine, IEEE, vol. 13, Nov. 1996, pp. 47-60.

Yan Yang et al., "Knowledge-Based 3D Segmentation and Reconstruction of Coronary Arteries Using CT Images", Engineering in Medicine and Biology Society, 2004, IEMBS '04, 26$^{th}$ Annual International Conference of the IEEE, pp. 1664-1666.

Danijela Vukadinovic et al., "Segmentation of the Outer Vessel Wall of the Common Carotid Artery in CTA", IEEE Medical Imaging, vol. 29, No. 1, Jan. 2010, pp. 65-76.

* cited by examiner

US 8,958,618 B2

METHOD AND SYSTEM FOR IDENTIFICATION OF CALCIFICATION IN IMAGED BLOOD VESSELS

BACKGROUND OF THE INVENTION

The present invention relates to the detection of calcification and the segmentation of vessel lumen and vessel walls in three-dimensional volume data sets obtained by medical imaging procedures such as computed tomography (CT).

CT scanning and other three-dimensional patient imaging techniques such as magnetic resonance imaging yield large image data sets comprised of three-dimensional arrays of voxels. Each voxel has a value indicative of the tissue type present at the corresponding location in the patient's body. In a CT data set the voxels have values defined in Hounsfield units (HU), representing the density of the tissue to the X-rays used to record the image.

When analysing the data set for research or diagnostic purposes, it is necessary to identify which voxels correspond to which types of tissue, so the voxels can be classified according to tissue type. Different organs and tissues can then be distinguished in the image. Subsequently, it is often desirable to be able to separate the voxels classified as being of a particular tissue type or organ from the remainder of the data set. This is known as segmentation. For example, in the procedure known as computed tomographic angiography (CTA), the blood vessels are of interest, so these need to be segmented from the data set as a whole. More specifically, coronary CTA records the coronary arteries, so these are segmented out of the data set. Furthermore, a coronary artery (in common with all blood vessels) is comprised of the vessel wall, being the various tissues of the wall itself including any deposits of plaque, and the lumen, being the blood-filled space bounded by the wall. Segmentation of both the lumen and the wall can be used to identify diseased regions of the vessel and is a diagnostic aid in cases of coronary artery disease. For example, accurate segmentation of lumen and wall is required in order to perform stenosis measurements, which can be part of a wider structural analysis of the coronary arteries imaged with CTA that aims to identify obstructions to vessel blood flow. Many automated techniques are available for segmentation, based on established values of HU intensity for different tissue types which enable a computer program to distinguish between voxels representing the lumen and voxels representing the vessel wall.

For success in these procedures, it is important to properly identify any deposits of calcium within the vessels. This identification can be difficult in coronary CTA images that are obtained in a contrast CTA scan, in which contrast dye is injected into a vein of the patient, and images are recorded as the dye circulates into the arteries. Calcium deposits tend to have a very similar HU intensity to that of the contrasted blood in the lumen. Hence it is difficult to tell calcium voxels apart from lumen voxels, which makes accurate segmentation difficult. For example, there are techniques that rely on a fixed HU threshold marking the boundary between calcium and blood to identify calcium deposits in an image and which operate satisfactorily to segment non-contrast enhanced CTA image data sets. This approach works less well in contrast CTA data, because there is no clear threshold between calcium and blood that can be selected in advance.

BRIEF DESCRIPTION OF THE DRAWINGS

Embodiments of the invention are now described by way of example only with reference to the following drawings.

DETAILED DESCRIPTION

Figure 1:
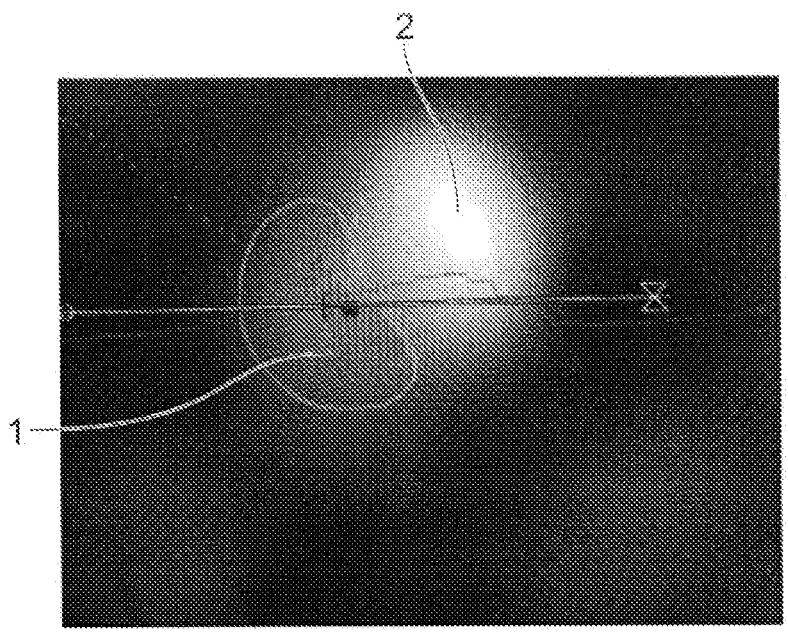
FIG. 1 shows a two-dimensional projection view through a contrasted coronary CTA three-dimensional image data set, including contrasted blood in a lumen and an adjacent calcium deposit.

Certain embodiments of the invention provide a computer system for and method of identifying calcification in a patient image data set showing one or more blood vessels. The computer system is operable to execute machine readable instructions for carrying out a method comprising: obtaining an image data set comprising voxels each having an intensity value; forming the intensity values into a group of intensity values, the intensity values covering an intensity range; defining a plurality of intensity thresholds with values spaced across the intensity range and including the end values of the intensity range; for each of the plurality of intensity thresholds partitioning the group of intensity values into two subgroups according to the intensity threshold, and calculating an information criterion as a function of the intensity threshold; generating an information criterion measure curve, being a plot of the calculated information criteria against intensity threshold; and locating a maximum in the information criterion measure curve and setting the corresponding intensity threshold to be a calcification threshold. The group of intensity values is then partitioned into two sub-groups using the calcification threshold, thereby identifying the voxels corresponding to the intensity values in the sub-group above the calcification threshold as representing calcification in the patient. The method may further comprise outputting to a user an indication of those voxels identified as representing calcification in the patient.

The information criterion may be the Bayesian information criterion, the Akaike information criterion, or the covariance information criterion, for example.

The method is widely applicable to image data obtained by a variety of imaging regimes. In particular the image data set may be a contrast computed tomographic angiography image data set, so that lumen of the one or more blood vessels contain contrast-enhanced blood, or the image data set may be a non-contrast computed tomographic angiography image data set, so that lumen of the one or more blood vessels contain non-contrast-enhanced blood. The image data set input to the method may be obtained by segmenting voxels from a patient image data set to obtain an image data set including a blood vessel of interest. For example, the segmenting may comprise removing all voxels with intensities below a predetermined threshold to leave voxels corresponding to calcification and lumen.

After identification of voxels representing calcification, the method may further comprise segmenting the voxels representing calcification from the image data set.

After this removal of the calcium voxels, embodiments propose a classification of vessel wall and lumen by assigning tissue-type probabilities to the voxels, in which case the method may further comprise dividing the voxels of the image data set that correspond to the one or more blood vessels into one or more segments along the vessel length; grouping adjacent segments together to form one or more regions; for each region applying a kernel across the region to assign a weight to each segment in the region, applying the weights to the intensity values of the voxels in the region to obtain a set of weighted voxel values, assuming a multiple-class statistical distribution of the weighted voxel values, the classes being voxels representing lumen and vessel wall components, and calculating a probability that each voxel represents each class using a classification algorithm operating on the multiple-class statistical distribution; and assigning probabilities of each class to each voxel according to the calculated probabilities. Further, the classification may be used to segment the voxels representing the lumen or the vessel wall from the image data set.

The adjacent segments may be grouped to form overlapping regions. Any suitable kernel function may be used, such as a Gaussian kernel. Similarly, the multiple-class statistical distribution may be a Gaussian distribution. The classification algorithm may be an unsupervised classification algorithm may comprising one or both of the k-means algorithm and the expectation-maximization algorithm.

Additional embodiments propose segmentation of the vessel wall, where after assigning probabilities to the voxels, the method may further comprise: dividing the voxels of the image data set that correspond to the one or more blood vessels into a plurality of sections along the vessel length; for each section defining a tubular shape as a model of the outer surface of the vessel wall, setting the tubular shape to be a three-dimensional energy function comprising a first term that is a volume integral within the tubular shape of the probabilities assigned to each voxel, a second term that is a surface integral on the tubular shape of the surface normal component of the voxel intensity gradient, and a third term that is a surface integral on the tubular shape of the deviation of voxel intensity from the average voxel intensity on the surface, and fitting each tubular shape by minimizing the energy function; joining the sections to align the fitted tubular shapes into a total fitted tubular shape that models the outer surface of the vessel wall along the vessel length; and segmenting the voxels of the vessel using the total fitted tubular shape to distinguish the voxels of the vessel from other voxels.

The three dimensional energy function may be defined as $$\text{Energy} = A \int P(I) dv + B \oint \nabla I \cdot \hat{u} d\sigma / \oint d\sigma + C \oint (I_0 - I)^2 d\sigma / \oint d\sigma$$

where A, B and C are constants, the first term represents a volume integral within the tubular shape of the probability of the voxels being vessel wall P(I) and I is the voxel intensity; the second term is a surface integral on the tubular shape of the surface normal $\hat{u}$ component of the image intensity gradient $\nabla I$; and the third term is a surface integral on the tubular shape of the deviation of the voxel intensity I from the average intensity $I_0$ on the surface.

A useful shape for the tubular shape is an elliptical cylinder, although other 3D geometrical shapes may be used instead. The fitted tubular shapes may be aligned by applying constraints or a smoothing function between the sections.

Embodiments of the invention provide a non-transitory computer program product bearing machine-readable instructions for carrying out methods according to aspects of the invention.

Embodiments of the invention provide an image acquisition device loaded with and operable to execute machine readable instructions for carrying out methods according to aspects of the invention.

A computed tomography imaging procedure, such as coronary computed tomographic angiography (coronary CTA) yields large image data sets in the form of three-dimensional arrays of voxels. Each voxel has a value, for example in Hounsfield units (HU), that represents a property of the tissue type (typically the attenuating effect on the X-rays used to record the image) at the corresponding location within the patient. Different tissue types have different attenuating properties so the corresponding voxels have different values and can be distinguished within the data array. Once distinguished, different tissues can be segmented out of the data for closer attention. Tissue types that have HU values which differ by a large amount from the values of neighbouring tissue types can be segmented more easily, particularly using computer-implemented techniques.

The detection of calcium deposits in coronary arteries is of medical interest, and can be achieved in a non-contrast enhanced coronary CTA image data set by setting a voxel value threshold that divides typical values for calcium voxels from typical values for lumen voxels. However, in coronary CTA images obtained using a contrast dye injected into the patient's blood system, calcium voxels have a very similar HU value to voxels showing the contrasted blood in the lumen. Hence it is difficult to accurately identify calcification. This is further complicated by the fact that it is typically not known whether any calcium is present in a vessel.

FIG. 1 shows a view through a contrasted coronary CTA three-dimensional image data set, obtained by taking a two-dimensional projection or slice through the data set which is orthogonal to the centreline of an imaged vessel. Hence the vessel is shown in cross-section. This shows the similarity in appearance between the contrasted blood in the lumen 1 and an adjacent calcium deposit 2. Hence, a pre-selected threshold value may not operate accurately to distinguish the lumen from the calcium in a segmenting computer program.

An embodiment of the present invention proposes an alternative approach for determining a threshold that can be used to accurately distinguish calcification from contrasted blood in a coronary CTA image. The proposed technique is able to identify the optimal threshold boundary between calcium and contrasted blood.

According to the embodiment, the threshold is identified using a likelihood or information criterion, for instance the Bayesian Information Criterion (BIC). An information criterion is a statistical tool for model selection, which enables a model to be selected from a finite set of models by measuring the relative goodness, or likelihood, of fit of each model. For example, the BIC has been successfully used to determine the number of clusters in a given set of data (Q. Zhao et al, "Knee Point Detection in BIC for Detecting the Number of Clusters", *Advanced Concepts for Intelligent Vision Systems*, vol. 5259, pp. 664-673, 208).

In the present example, the model is a set of image data (voxels) partitioned by a threshold intended to divide voxels of calcium from voxels showing other tissue types, in particular lumen voxels. Voxels with an intensity (HU) value above the threshold are classified as calcium. The value of the threshold is not known in advance, so could have any of a range of values. These different possible threshold values give the finite set of models, with each model in the set having a different threshold. Application of the information criterion to each of the models allows identification of the model giving the best fit, namely the model in which the threshold best divides the calcium voxels from the other voxels.

Figure 2:
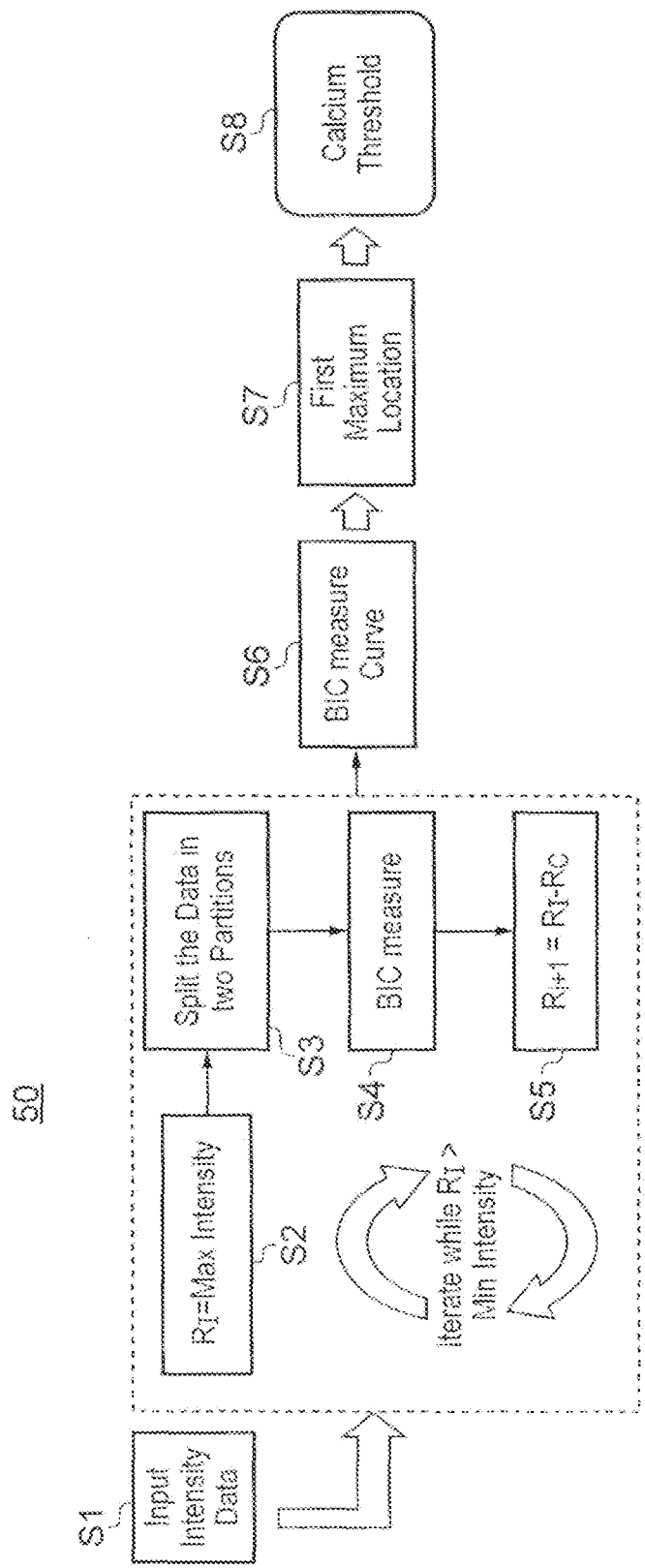
FIG. 2 shows a schematic representation of a method for identifying calcification according to an embodiment of the invention.

FIG. 2 shows a schematic representation of an embodiment of this method 50 for identifying calcification. Initially, it is necessary to gather the appropriate image data. For this, a patient can be newly scanned using the contrast CTA technique, or a previously recorded data set can be accessed. To avoid unnecessary data processing, the data corresponding to a region including the vessel of interest can then be extracted or segmented (using any known segmentation technique) from the remainder of the image data. Also, voxels with low intensity values which can be definitely identified as being neither calcium nor lumen can be removed. A suitable threshold value in Hounsfield units can be set to achieve this, selected from known typical values for other tissue types. If desired, the threshold can be sufficiently high so as to retain only those voxels corresponding to calcium or lumen. This processing gives a small subset of image data for efficient execution of the remainder of the method.

Each voxel in the subset will have a corresponding intensity value (for example, in HU). These intensity values are the data which are input into the method shown in FIG. 2, at step S1. The data can be organised as a list or group of intensities $L_{intensity}$, with one intensity value for each voxel in the subset.

In step S2, the method determines which is the maximum value of all the voxel intensity values in $L_{intensity}$. This is set as an initial threshold $R_I$, so that $R_I$=Max Intensity.

In step S3, the data group $L_{intensity}$ is partitioned into two partitions or subgroups according to the initial threshold $R_I$. So, all intensity values above $R_I$ are placed into a first subgroup, and all the intensity values below $R_I$ are placed in a second subgroup. At this stage, $R_I$ is set to the maximum intensity present in the data subset, so the first subgroup has no members and the second subgroup has all the intensity values as members.

In step S4, the BIC is calculated on these two partitions or subgroups, as a function of the threshold $R_I$. Calculation of the BIC is explained in more detail below.

It is assumed that within each partition, the intensity values have a particular probability distribution, so a suitable distribution is fitted to the data in each partition. The aim is to find the best separating threshold between the two distributions, as this will correspond to the boundary between the calcium and the lumen. Gaussian distributions may be used, for example, although other distributions may be chosen if more appropriate for a given data set. Also, the subgroup corresponding to the non-calcium voxels may be modelled by more than one distribution, for example a subgroup for vessel wall voxels and a subgroup for lumen voxels, which are themselves divided from one another by a predefined threshold. Hence, in such a case the data set is modelled using three distributions altogether, and the BIC calculation is used to find the threshold between the calcium and non-calcium voxels. Additional distributions could be incorporated if desired. In the event that multiple subgroups and distributions are used, the BIC is modified correspondingly, so that the BIC is calculated on the appropriate number of subgroups.

Proceeding to step S5, the initial threshold $R_I$ is reduced, by decreasing it by a constant $R_C$, thus: $R_i=R_I-R_C$.

The method then returns to step S3, and $L_{intensity}$ is repartitioned using the new threshold value. Subsequently, step S4 is repeated, so that the BIC is calculated on the two new partitions. Then, step S5 is repeated by again reducing the threshold value by the constant $R_C$.

The method continues to iterate through steps S3, S4 and S5 until the threshold falls below the minimum intensity value in $L_{intensity}$ (which means that further partitioning is not possible). So, iterate S3 to S5 while $R_I$>Min Intensity. The result of the iteration is a set of BIC measures, one for each iteration of the steps S3 to S5.

Calculation of the BIC will now be explained in more detail. First, we define

RI=Initial partitioning threshold
RF=Final partitioning threshold
ΔR=Partitioning threshold change $$Rk=RI \text{ for } k=0$$

$$CA=\{n \epsilon I : n < Rk\}$$

$$CB=\{n \epsilon I : n > Rk\}$$

$$Ci=\{CA, CB\}$$

$$m=|Ci|$$

where I=Set of input intensities, and Ci=Set of partitions based on the current threshold Rk, which is changed by a small ΔR in every iteration of the algorithm.

$$R_{k+1} = R_k - \Delta R, \text{ until } R_{k+1} \leq RF$$

$$ni = \{|CA|, |CB|\}$$

$$mi = \{\mu CA, \mu CB\}$$

$$Vi = \frac{1}{ni-m} \sum_{j=i}^{ni} \|xj - mi\|^2$$

where ni=number of samples in each partition, m=number of partitions, mi=mean of each partition, Vi=variance estimate for each partition i, xj=jth point in a partition.

The data is partitioned into two groups: calcium voxels and non-calcium voxels, so m=2.

Now, the BIC is calculated for every iteration k:

$$BIC = \sum_{i=1}^{m}\left(n i \log n i - n i \log n - \frac{ni*d}{2}\log(2\pi) - \frac{ni}{2}\log Vi - \frac{ni-m}{2}\right) - \frac{1}{2}m\log n$$

where d=data dimension.

As the end result, the sought-after calcium threshold is the partitioning threshold Rk which generated the highest value of the BIC.

So, once the iteration across the intensity range of $L_{intensity}$ is complete, the method proceeds to step S6. In step S6, the set of BIC measures is used to generate a BIC measure curve, which is a graph of BIC measure against the threshold value $R_I$ used to calculate that BIC measure.

Figure 3:
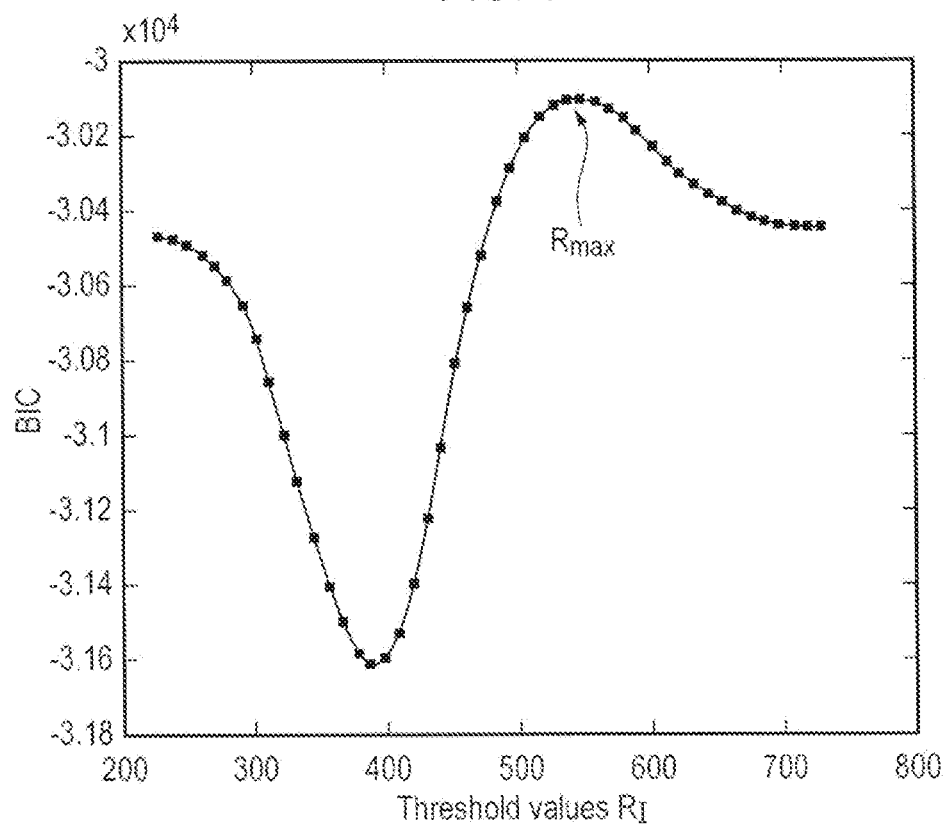
FIG. 3 shows an example of a Bayesian information criterion measure curve generated by a step in the method of FIG. 2.

FIG. 3 shows an example BIC measure curve, as produced by step S6.

In step S7, the method identifies the location of the first maximum on the BIC measure curve. This is indicated by the arrow in FIG. 3. In some embodiments, the maximum may be other than the first maximum, and may be the highest-valued maximum.

Finally, in step S8 the threshold value $R_{max}$ corresponding to the first maximum is taken to be the intensity value threshold that best partitions the voxel subset into calcium voxels and non-calcium voxels (typically lumen voxels). Hence, the calcium threshold has been determined.

Using this threshold, it is now possible to identify those voxels in the image data that correspond to calcium deposits. Hence, calcification can thereby be detected. Further, once detected, the calcification can be segmented from the image data, which then allows more accurate segmentation of the lumen and the vessel wall. For enhanced accuracy, it is recommended that the procedure of FIG. 2 is repeated for all vessels of interest within the image data set. This allows for background variations in intensity through the data set, and any local fluctuations or artefacts. In some circumstances, however, the same threshold $R_{max}$ might be applied across the data set to identify all calcium deposits. Alternatively, $R_{max}$ thresholds might be calculated for a small sample of vessels, and an average value, minimum value, or other combination of values then applied to the whole data set. Otherwise, though, a threshold may be applied only to the particular vessel, sample of vessels, or part of a vessel from which it is calculated.

The method of identifying calcification according to the present embodiment may be summarised as follows:

(a) receive as an input an image data set comprising voxels each having an intensity value;

(b) form the intensity values into a group of intensity values, the intensity values covering an intensity range;

(c) define an intensity threshold with a value corresponding to a first end value of the intensity range;

(d) partition the group of intensity values into two subgroups according to the intensity threshold;

(e) calculate an information criterion on the two subgroups as a function of the intensity threshold;

(f) adjust the intensity threshold by a constant;

(g) repeat steps (d) to (f) until the intensity threshold reaches a second end value of the intensity range;

(h) generate an information criterion measure curve, being a plot of information criterion against intensity threshold;

(i) locate the first maximum in the information criterion measure curve and set the corresponding intensity threshold to be a calcification threshold; and (j) partition the group of intensity values into two subgroups using the calcification threshold, thereby identifying the voxels corresponding to the intensity values in the subgroup above the calcification threshold as representing calcification in the patient.

In the example illustrated in FIG. 2, the intensity threshold is reduced by the constant $R_C$ in each iteration. The size of the constant will determine the number of values attributed to the intensity threshold, and hence the number of iterations carried out, and can therefore be selected as desired. A greater number of iterations gives a greater number of BIC measures, giving a smoother BIC measure curve and hence a potentially more accurate final result, but this will need to be balanced against available processing time and resources. If sufficient resources are available, it may be desirable to determine the full range of threshold values $R_I$ from Max Intensity to Min Intensity at the outset, and then execute the data partitioning of step S3 and the BIC calculation of step S4 for each threshold in parallel. Also, an equivalent result will be obtained if the initial threshold RI is set to be the minimum intensity, and the iteration is performed by increasing the threshold by the constant for each iteration so that $R_i=R_i+R_C$. This is carried out until the maximum intensity value is reached, in other words, iterate while $R_I$<Max Intensity.

As an alternative to starting at one end of the intensity value range and stepping through the range by a constant until the other end is reached, the set of intensity threshold values can be obtained simply by dividing up the range of intensity values. Further, it is not necessary that the intensity threshold values be equally spaced across the intensity range, such as will result from stepping by a constant. If there is any a priori knowledge of the expected location of the calcification threshold, the intensity thresholds can be clustered most closely around this point, and more widely spaced over other parts of the range. Under these non-iterative approaches, all the thresholds can be defined in advance before the partitioning and BIC calculations are performed.

As noted, the calcium threshold is taken to be the threshold corresponding to one of the local maxima of the BIC curve. Consequently, any procedure for finding a suitable maximum can be used; the invention is not limited to the techniques described herein.

Figure 4A:
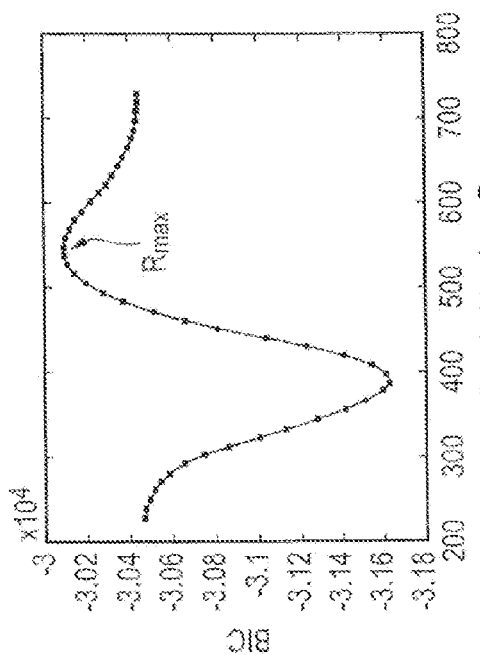
FIGS. 4A and 4B show a first example of voxel intensity data to which the method of FIG. 2 has been applied, and the calcium threshold identified by using the method.
Figure 4B:
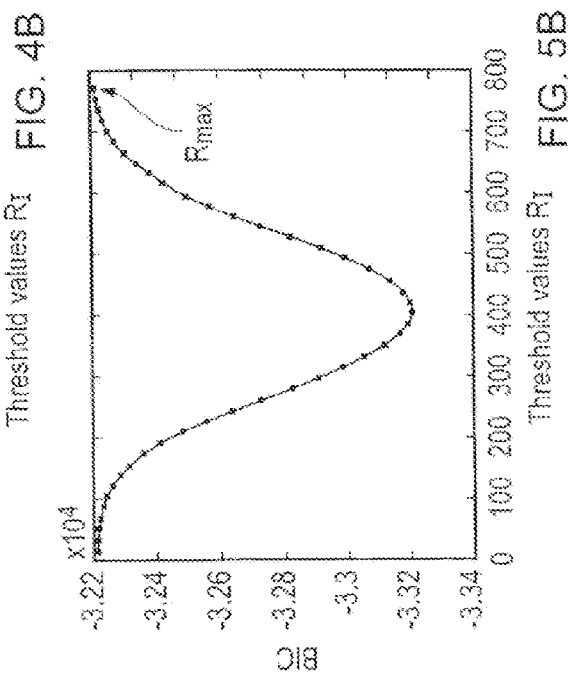

FIGS. 4A and 4B show a first example of voxel data subjected to the method of FIG. 2, and the resulting identified threshold. FIG. 4A shows a histogram of the intensity values of voxels in the input data set. Hence, all voxels represented in FIG. 4A make up the intensity list $L_{intensity}$. In this example, the blood within the lumen has been contrasted, and some calcification is present, at a level of 3.6% of the total number of voxels representing blood. The mean intensity value for the contrast blood voxels is 400 HU with a standard deviation of 100. The mean intensity for the calcium voxels is 650 HU with a standard deviation of 60.

FIG. 4B shows the BIC measure curve obtained by applying the method of FIG. 2 to the data of FIG. 4B. The first maximum of the curve corresponds to a threshold value of 564.1 HU. If this is applied to the data of FIG. 4B, it can be seen to correctly divide the contrasted blood voxels from the calcium voxels, being both above the mean blood intensity plus standard deviation (400+100=500 HU) and below the mean calcium intensity minus standard deviation (650−60=590 HU).

Figure 5A:
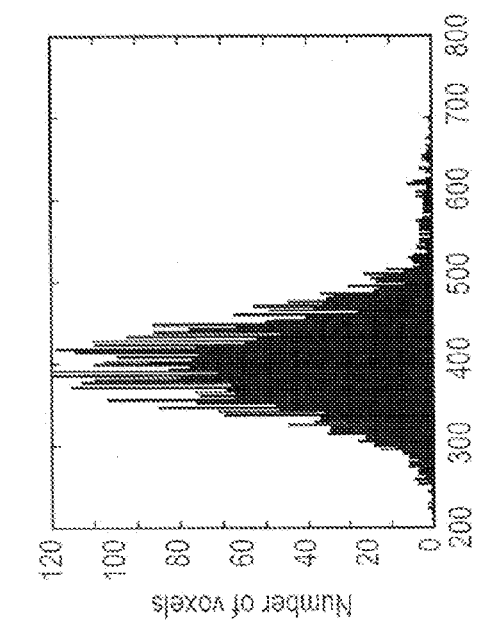
FIGS. 5A and 5B show a second example of voxel intensity data to which the method of FIG. 2 has been applied, and the calcium threshold identified by using the method.
Figure 5B:
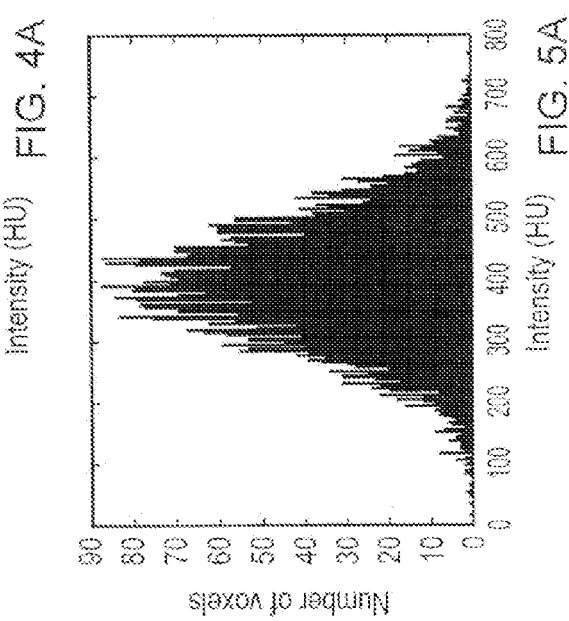

FIGS. 5A and 5B show a second example. FIG. 5A shows a histogram of voxel intensity values in the input data set. In this example, the mean intensity for the contrasted blood voxels is 400 HU with a standard deviation of 200. No calcification is present.

FIG. 5B shows the BIC measure curve calculated for the data of FIG. 5B. The first maximum of the curve is at the maximum intensity for the data set, being 774 HU. Again, this threshold will correctly partition the voxels, because all voxels will have intensity values below the threshold so will not be removed in any segmentation. This is the desired outcome for a sample in which no calcium is present.

These examples show good results for contrast coronary CTA images, even in cases where the proportion of one tissue type is only a small fraction of the other such as the FIG. 4 example where the calcium is a mere 3.6% of the blood. It is further expected that the method will be equally applicable to non-contrast enhanced CT data sets. Hence, the method according to this embodiment gives a reliable and accurate technique for identifying and segmenting calcification in both contrast and non-contrast CT images, and is hence a great improvement over existing techniques that operate for non-contrast images but fail for contrast images.

A further advantage of the method is that, unlike many existing techniques for tissue classification, it does not require any training. Such trained classifier techniques are laborious because they require the acquisition of many example data sets which are then manually classified, and used to train a software-based classifier which should then be able to correctly classify a new sample data set. Incorrect classification can occur if the sample is too unlike any of the training examples, however, and other errors arise from intensity variations across the set of training examples arising from different imaging devices and conditions. The present invention is able to correctly operate upon a single isolated data set without reference to any other. It is therefore much more efficient to implement, and operates independently of any imaging variations.

While the above examples have used BIC, the invention is not so limited. Other statistical techniques for model selection may also be used. For example, other information criterion may be used, including the Akaike information criterion (AIC) and the covariance [POSSIBLY COPULA?] information criterion.

It is intended that the methods of the embodiments of the present invention be implemented on a computer. The methods may execute on a suitably programmed general purpose computer workstation, for example, which may be a computer operating in a hospital or other medical environment, perhaps as part of a network.

Figure 6:
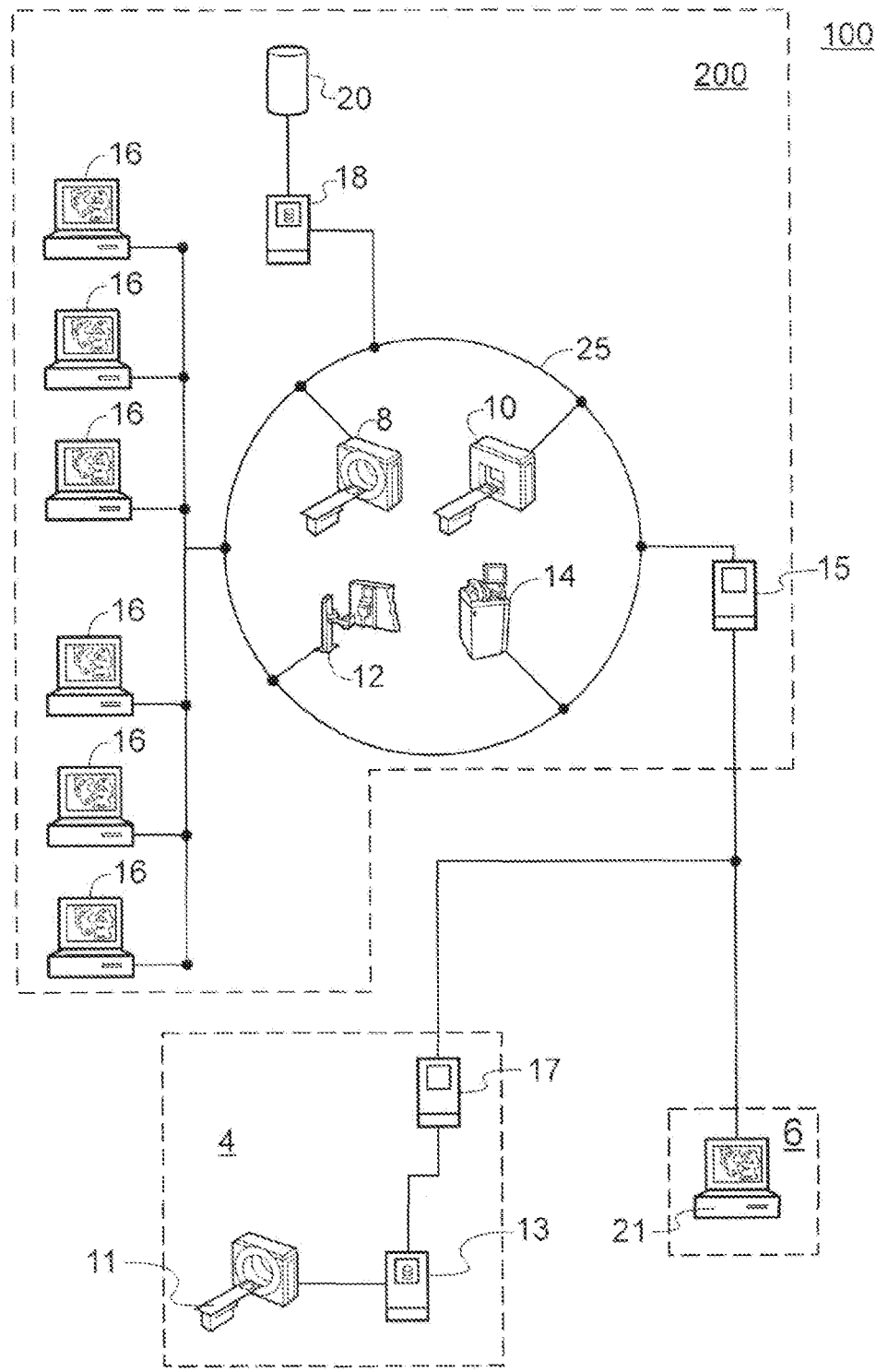
FIG. 6 is a schematic representation of an exemplary network of computer controlled diagnostic devices, stand-alone computer workstations and associated equipment.

FIG. 6 is a schematic representation of an example of such a network 100, including computer controlled diagnostic devices, stand-alone computer workstations and associated equipment. The network 100 comprises three components. There is a main hospital component 200, a remote diagnostic device component 4 and a remote single user component 6. The main hospital component 200 comprises a plurality of diagnostic devices for acquiring patient images, in this example, a CT scanner 8, a MR imager 10, a DR device 12 and a CR device 14, a plurality of computer workstations 16, a common format file server 18, a file archive 20 and an internet gateway 15. All of these features are inter-connected by a local area network (LAN) 25.

The remote diagnostic device component 4 comprises a CT scanner 11, a common format file server 13 and an internet gateway 17. The CT scanner 11 and file server 13 are commonly connected to the Internet gateway 17, which in turn is connected via the Internet to the Internet gateway 15 within the main hospital component 200.

The remote single user component 6 comprises a computer workstation 21 with an internal modem (not shown). The computer workstation 21 is also connected via the internet to the internet gateway 15 within the main hospital component 200.

The network 100 may be configured to transmit data within a standardized common format. For example, the CT scanner 8 initially generates a source data set, i.e. a 3D volume image data set comprising an array of voxels, from which an operator may derive one or more 2D images. The 2D image is encoded in a standard image data format and transferred over the LAN 25 to the file server 18 for storage on the file archive 20. A user working on one of the computer workstations 16 may subsequently request retrieval of the image. In response, the file server 18 will retrieve it from the archive 20 and pass it to the user via the LAN 25.

Similarly, a user working remotely from the main hospital component 2 may also access and transmit data stored on the archive 20, or elsewhere on the network 1. Access may be either within the remote diagnostic device component 4, or within the remote single user component 6. Also, the archive 20 can store the original 3D volume data set for subsequent retrieval and transmittal to any of the workstations 16, 21.

The computer workstations 16, 21 preferably have access to software configured to conform to the common image data format. The standardization of the image data format ensures that different software applications on the computers 16, 21, the file servers 13, 18 and file archive 20 and the output from the different computer controlled diagnostic devices 8, 10, 11, 12, 14 can share image data. A user such as a radiologist, a consultant, or a researcher can access any volume data set from the file archive 20 using the computer workstations 16, 21 and generate and display movies or other images, such as a still image of a 3D data set or moving images from a 4D data set. In particular, one or more of the workstations 16, 21 is provided with software configured to implement the methods of the embodiments of the present invention.

The methods of these embodiment may usefully be integrated into a stand-alone software application, or with a Picture Archiving and Communication System (PACS). A PACS is a hospital-based computerized network which can store volume data representing diagnostic images of different types in a digital format organized in a single central archive. The most common image data format currently employed for medical applications is the "Digital Imaging and Communications in Medicine" format, usually referred to as DICOM. The DICOM standard is published by the National Electrical Manufacturers' Association of America. Each image has associated patient information.

Figure 7:
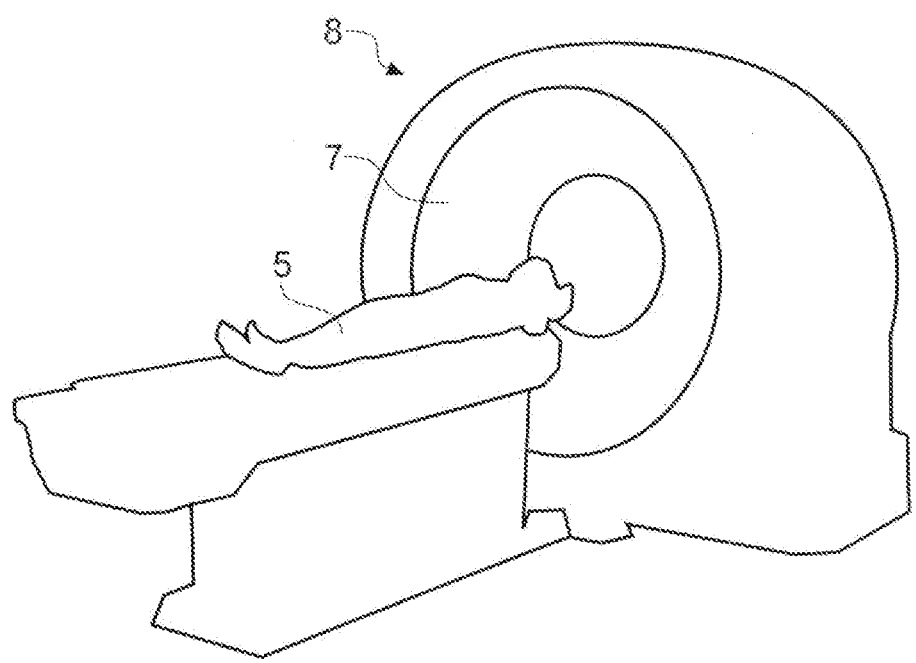
FIG. 7 shows a generic computer-assisted tomography (CT) scanner for generating image volume data.

FIG. 7 is a schematic perspective view of a generic scanner, most especially a CT scanner 8, for obtaining a 3D X-ray scan of a region of a patient 5. The relevant part of a patient's body, in the case of coronary CTA scanning being the chest including the heart, is placed within a circular opening 7 of the scanner 8. A series of image slices through the patient's abdomen is recorded, or alternatively a single spiral image, depending on the scanner type. Raw image data are derived from the scanner, which in the case of image slices could comprise a collection of one thousand 2D 512×512 data subsets, for example. These data are combined to produce the 3D volume data set, which makes up a 3D image data set, comprise a collection of voxels, each with a value corresponding to the X-ray attenuating characteristic of the corresponding tissue type in the patient. Thus the volume data are a 3D representation of the feature imaged. If desired, various user-selected 2D projections (output images) of the 3D representation can be displayed, typically on a computer monitor. 3D and moving 4D representations can also be displayed. Often, it is desired to concentrate on one or more tissue types of particular interest. To achieve this, the voxels corresponding to these tissue types are segmented, or extracted, from the data set, for example by using the tissue classification and segmentation techniques of the embodiments of the present invention.

Figure 8:
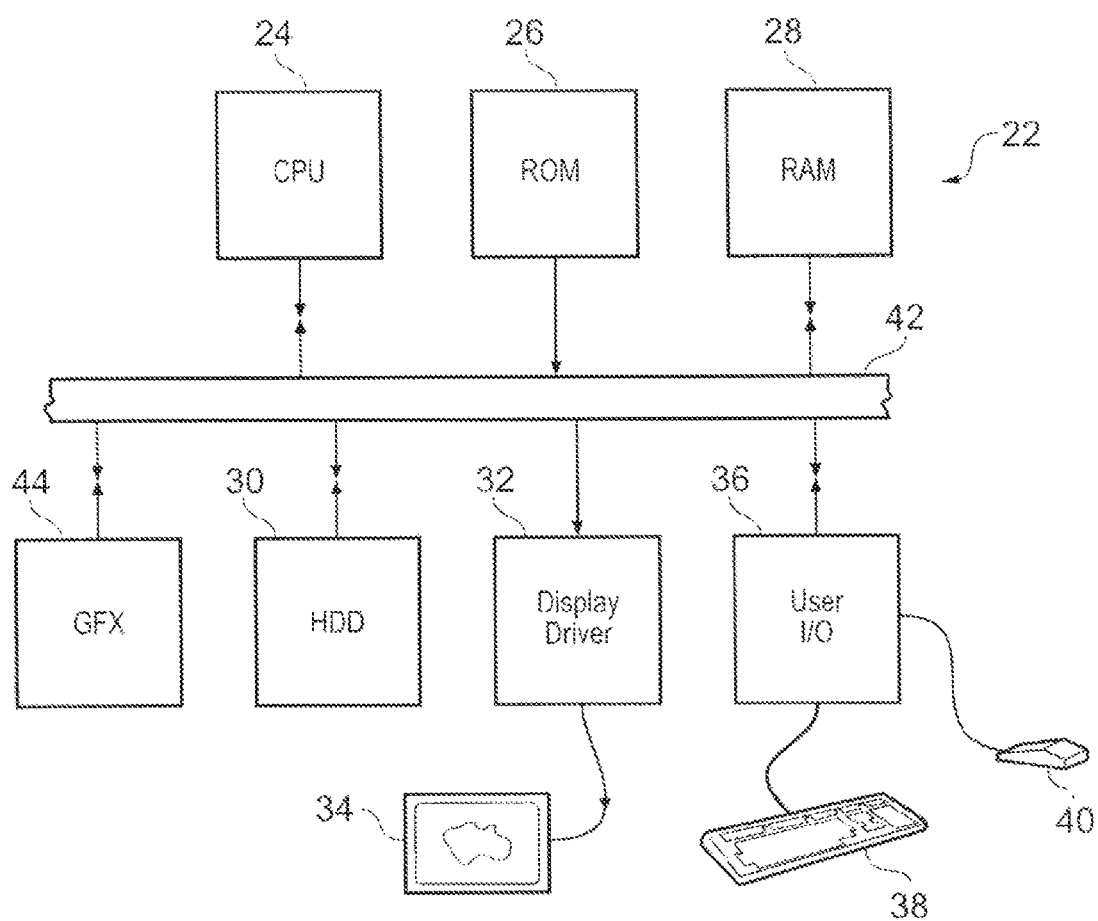
FIG. 8 schematically shows a computer for processing image volume data.

FIG. 8 schematically illustrates a general purpose computer system 22 configured to perform processing of volume data, for example in accordance with embodiments of the present invention. The computer 22 includes a central processing unit (CPU) 24, a read only memory (ROM) 26, a random access memory (RAM) 28, a hard disk drive 30, a display driver 32 and display 34 and a user input/output (IO) circuit 36 with a keyboard 38 and mouse 40. These devices are connected via a common bus 42. The computer 22 also includes a graphics card 44 connected via the common bus 42. The graphics card includes a graphics processing unit (GPU) and random access memory tightly coupled to the GPU (GPU memory) (not shown in FIG. 8).

The CPU 24 may execute program instructions stored within the ROM 26, the RAM 28 or the hard disk drive 30 to carry out processing of signal values associated with voxels of volume data that may be stored within the RAM 28 or the hard disk drive 30. The RAM 28 and hard disk drive 30 are collectively referred to as the system memory. The GPU may also execute program instructions to carry out processing of volume data passed to it from the CPU.

Figure 9:
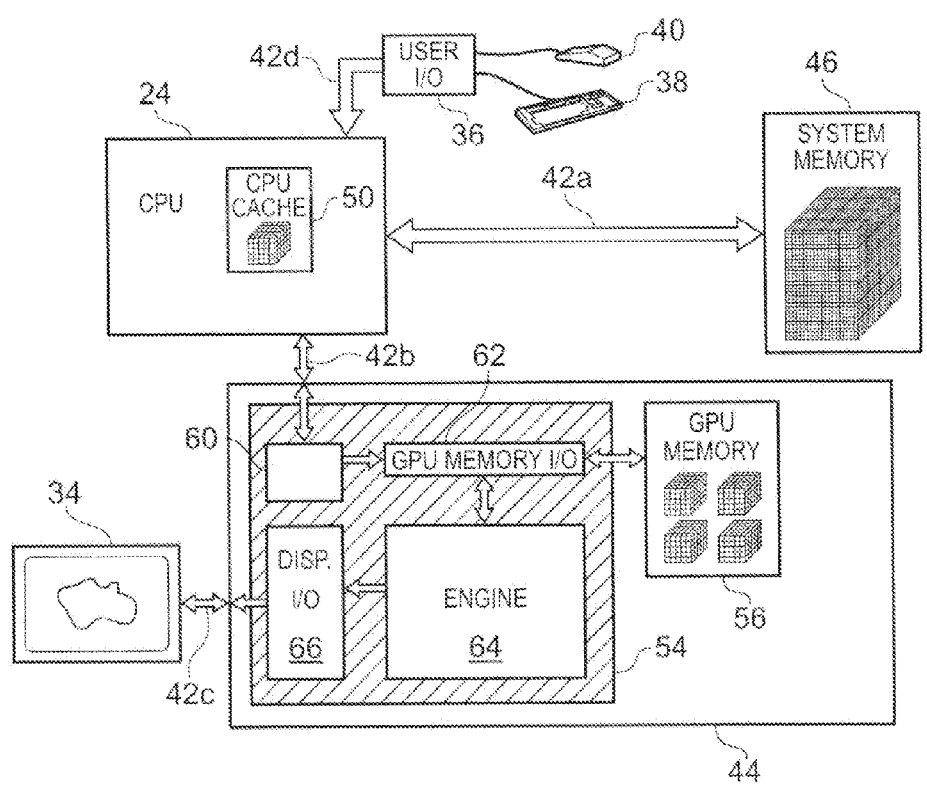
FIG. 9 schematically shows some of the features of the computer of FIG. 6 in more detail.

FIG. 9 schematically shows some of the features of the computer system shown in FIG. 8 in more detail. The RAM 28 and hard disk drive 30 are shown collectively as a system memory 46. Volume data obtained from the scanner 8 shown in FIG. 6 is stored in the system memory as shown schematically. Any suitable form of mass storage device may be used. To assist in showing the different data transfer routes between features of the computer system 22, the common bus 42 shown in FIG. 8 is schematically shown in FIG. 9 as a series of separate bus connections 42a-d. A first bus connection 42a connects between the system memory 46 and the CPU 24. A second bus connection 42b connects between the CPU 24 and the graphics card 44. A third bus connection 42c connects between the graphics card 44 and the display 34. A fourth bus connection 42d connects between the user I/O 36 and the CPU 24. The CPU includes a CPU cache 50. The graphics card 44 includes a GPU 54 and a GPU memory 56. The GPU 54 includes circuitry for providing an accelerated graphics processing interface 60, a GPU cache I/O controller 62, a processing engine 64 and a display I/O controller 66. The processing engine 64 is designed for optimized execution of the types of program instructions typically associated with processing 3D image data sets and carrying out 3D rendering of such data sets. The processing unit thus comprises CPU and GPU elements.

The user is able to select desired visualization parameters using the keyboard 38 and mouse 40 in combination with a graphical user interface (GUI) displayed on the display 34, for example using a movable screen icon in combination with a mouse, track pad etc. to point and click, a touch screen or other known techniques.

The above-discussed embodiments for identifying calcium deposits in blood vessels can be used as part of other techniques for classifying tissue types in an image data set and/or segmenting those tissue types from the bulk of the data set. Continuing the example of an imaged blood vessel, where the image might be obtained by contrast or non-contrast CTA, a common task is to identify the voxels representing the wall of the vessel, and the voxels representing the lumen containing blood. In other words, the voxels are classified according to tissue type. This is particularly relevant in the diagnosis of coronary artery disease where the goal is to detect obstructions to vessel blood flow. In the first instance, this requires accurate segmentation of lumen and vessel wall in order to perform stenosis measurements. It is advantageous to be able remove calcification voxels from the data set as a preliminary stage in the image processing, to enable more accurate lumen/wall segmentation.

Figure 10:
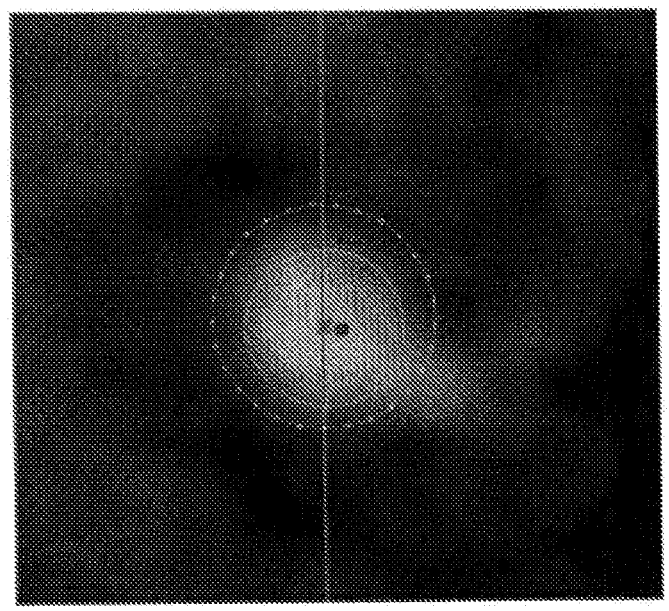
FIG. 10 shows a two-dimensional projection of a volume image data set of a blood vessel.

FIG. 10 shows a 2D projection of a 3D image data set of a blood vessel. The vessel is seen in transverse cross-section. The solid line shows the outer edge of the lumen, filled with blood, and being the boundary where the lumen and vessel wall meet. The dotted line shows the outer edge of the vessel wall. Hence all voxels between the two lines correspond to vessel wall, and the voxels inside the solid line correspond to lumen/blood.

The classification of voxels into particular tissue types can be difficult. The different tissue types appear in the image as voxels with different intensities, but the intensities for any given tissue type can vary due a range of factors including differences in image acquisition hardware, anatomical variations in the patient, the presence of diseased regions, the medical protocol used when injecting the patient with any contrast dyes or agents, and attenuation caused by the contrast dye.

Figure 11:
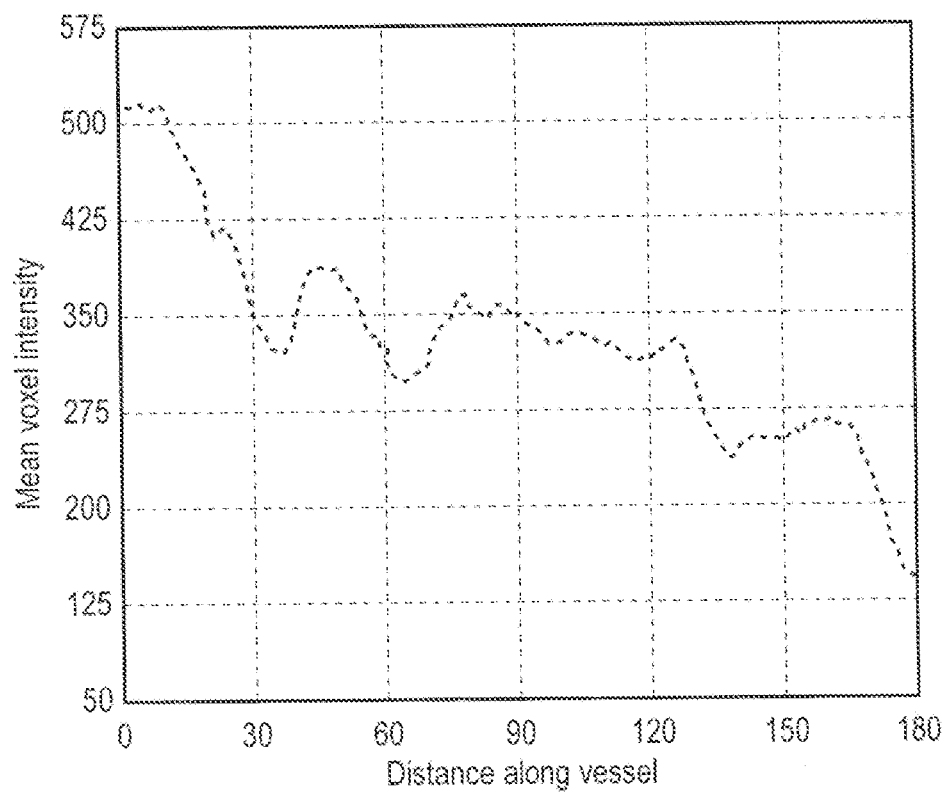
FIG. 11 shows a graph of mean lumen voxel intensity against distance along a blood vessel for a contrast-enhanced image.

FIG. 11 shows a graph to illustrate this last point. The graph shows the mean intensity of lumen voxels against distance along a blood vessel, for a contrast-enhanced image. As can be seen, the intensity decreases markedly along the vessel length, according to changes in the attenuation of the contrast agent. Hence, any attempt to classify the lumen voxels by setting a simple intensity threshold above which voxels are classified as lumen will fail.

Some tissue classification techniques rely on supervised learning. These are techniques in which a large number of data sets are manually classified by clinicians or other medical professionals, and then input into a computer classification program as training data (also known as ground truth). The inputs are mapped to the outputs of the known tissue types, and from the appearance of different images types, the program "learns" to recognize different tissue types so can classify newly input image data. However, the above-noted intensity variations are difficult to correctly model in supervised learning. A large number of data sets showing a large number of variations is required, and it is difficult to generalize the results to differing anatomical regions. Also, the training data can potential bias the results.

Unsupervised classification techniques are an attractive alternative that do not require large sets of training data. Unsupervised learning aims to model the imaged tissue from the input data using statistical methods, without reliance on any mapping to known outputs. The output is typically in the form of a probability or likelihood that any given voxel represents a particular tissue type. Algorithms used include the k-means algorithm and the expectation-maximization (EM) algorithm.

An embodiment of the present invention aims to improve the application of known unsupervised techniques for tissue classification, by assigning a probability of each tissue type to each voxel in a data set of interest.

Figure 12:
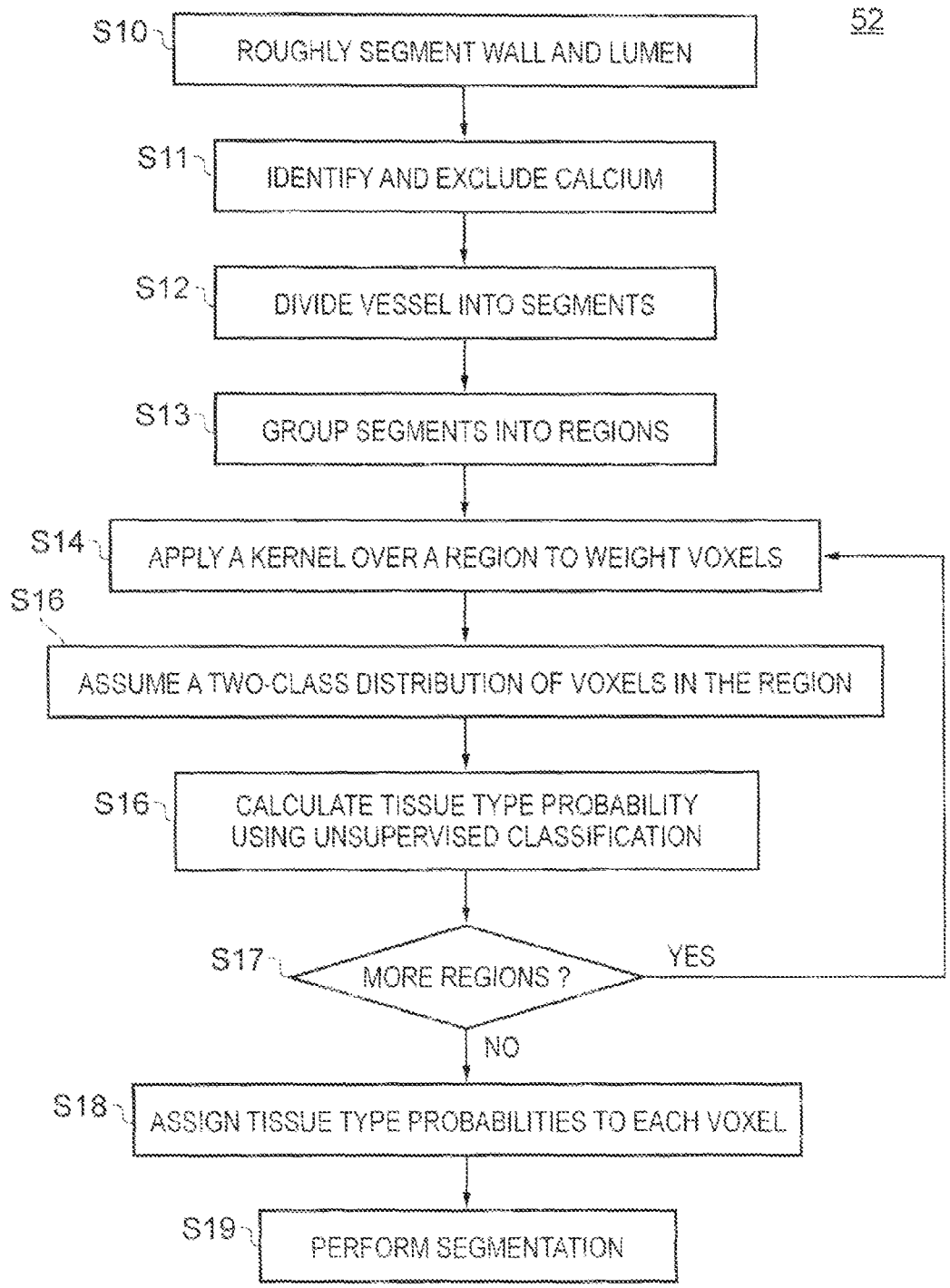
FIG. 12 shows a flow chart of a method for applying tissue-type probabilities to tissue voxels according to an embodiment of the invention.

FIG. 12 shows a flowchart of an example method 52 of tissue probability classification, applied to an imaged blood vessel.

The method commences at step S10, in which the voxels of a blood vessel are roughly segmented from their image data set using, for example, an efficient active contour algorithm. The final results of the probability classification do not strongly depend on this initial approximate segmentation, so any desired segmentation technique can be used. The aim is to produce a set of voxels substantially corresponding to the vessel only, that is the wall and the lumen, plus any calcification that may be present. Some tissue surrounding the vessel may also be included without detriment.

Next, in step S11, any voxels representing calcium are identified and excluded from the set of voxels, for example by using the calcification identification method 50 described above with reference to FIG. 2. Note that this step is optional. For example, it may be known or assumed that no calcification is present, or the presence of any calcification may be considered unimportant.

In step S12, the vessel as represented by the remaining voxels is divided into a plurality of segments along the length of the vessel. The segments may be arbitrarily small, so the total number of segments may be selected with reference to factors such as the desired processing time and the length of the vessel of interest. For example, the segments may be around a voxel in thickness. The segments may or may not be all of equal thickness.

Figure 13:
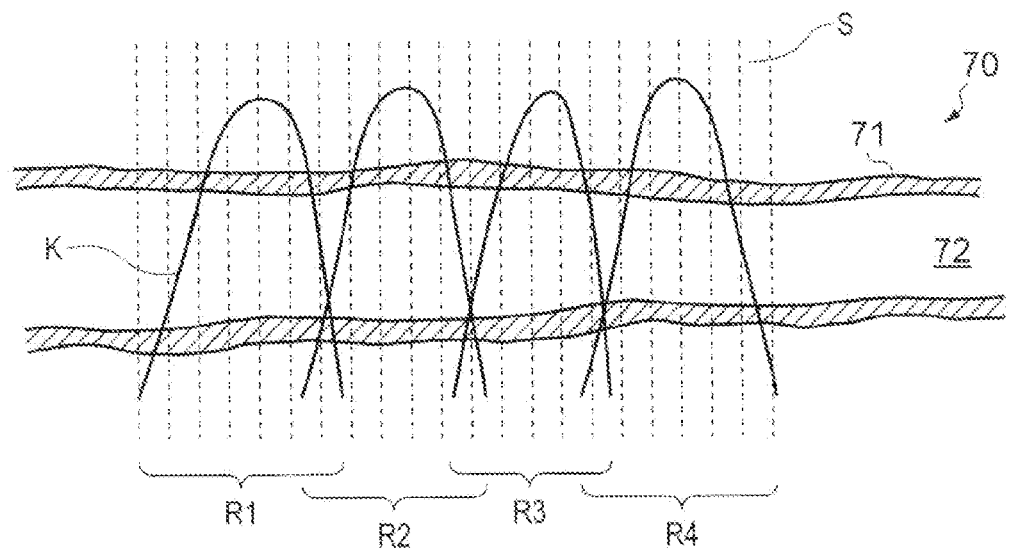
FIG. 13 shows a schematic representation of an imaged blood vessel to which steps of the method of FIG. 12 have been applied.

FIG. 13 shows a schematic cross-section through part of an imaged blood vessel 70, comprising a vessel wall 71 and a lumen 72. In accordance with step S12, the vessel has been divided into a plurality of adjacent segments S, indicated by the dotted lines.

Then, in step S13, adjacent segments are grouped together into regions. The number of segments in each region can be chosen as desired. For example, FIG. 13 shows the segments S grouped together into regions R1, R2, R3, R4 each comprising six segments. A useful range of number of segments per region has been found to be between about 3 and 10 segments, but other amounts of segments are not precluded. Also, the segments can be grouped such that the regions overlap, as in the example of FIG. 13. The amount of overlap can be chosen as desired. In FIG. 13, the regions overlap by one segment. The presence of an overlap permits a smooth transition between the regions. For this, the overlap is preferably small compared to the length of the regions, so that the boundaries of each region are included in adjacent regions but the bulk of the regions are independent. However, the method may be implemented with no overlap.

Moving to step S14, a kernel is applied across each region. Kernels K are shown in FIG. 13. A Gaussian kernel can be used, although other kernel functions may be used instead, such as uniform, triangular, quartic, cosine or triweight. A kernel is a weighting function. Hence, the application of the kernel across the region enables a weight to be applied to the intensity value of each voxel. The weighting is performed on a per-segment basis, so that all voxels in each segment within the region are given the same weight. The weighting thus produces a set of weighted voxel values, with the voxels in the central parts of the region weighted more heavily that the voxels in the end parts of the region.

Once the weighting is applied, the method moves onto a probability classification of the voxels in that region, in steps S15 and S16. The method uses a multiple-class statistical approach to achieve unsupervised probability assignments. Hence, in step S15, the set of weighted voxels values are assumed to have a two-class statistical distribution, where the two classes are voxels representing vessel wall and voxels representing lumen. A Gaussian distribution can be assumed for each class, although other statistical distributions may be used if preferred. Gaussian distributions tend to give good classification results, however. Also, more than two class can be assumed, if desired, where each class corresponds to a different vessel tissue component or type.

Figure 14:
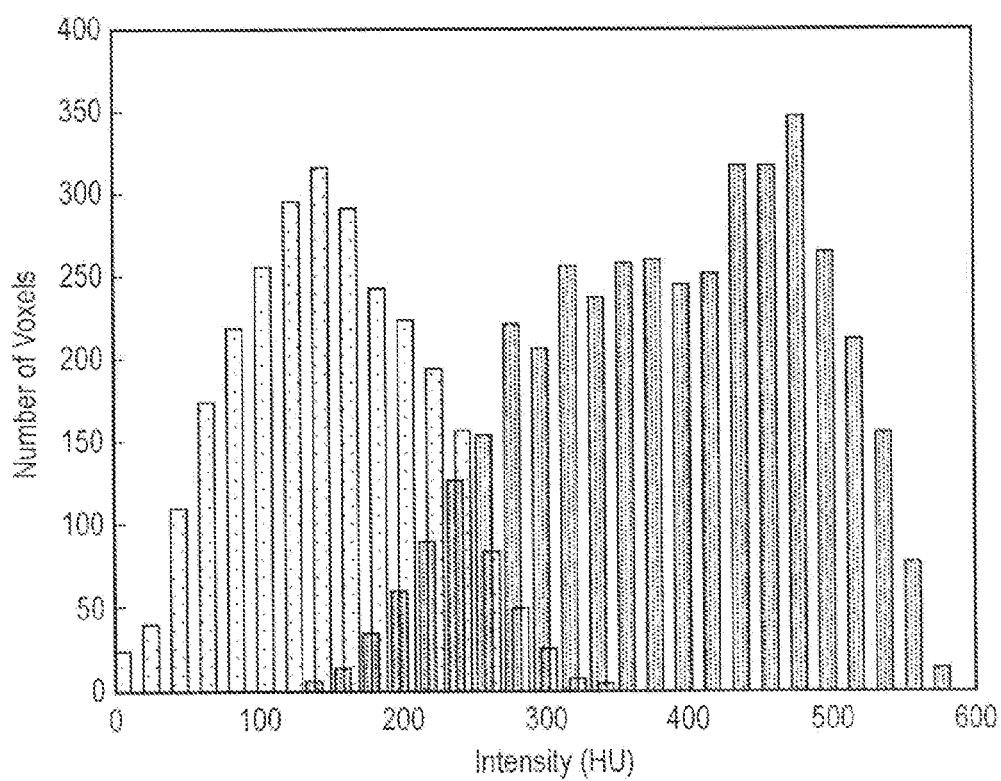
FIG. 14 shows a histogram of voxel intensity for an example data set of lumen and vessel wall voxels which may be classified using the method of FIG. 12.

FIG. 14 shows a histogram of voxel intensity for an example data set of lumen and vessel wall voxels. The voxels representing lumen have in general a higher intensity than those representing vessel wall, but within each of the two groups or classes the voxels have a distribution of intensities over a substantial range. Further, the two ranges overlap, so it is not straightforward to classify the voxels into the two classes. According to the assignment of probabilities according to the present embodiment, a probability for each tissue type or class is assigned to each voxel, giving multiple probability values per voxel. Near the peak of each distribution, the probability for one class is much greater than for the other class. In the regions of overlap, the probability for each class will be similar.

As mentioned, in step S15, a particular two (or more)-class statistical distribution is assumed for the different groups of voxel intensities, in this example a Gaussian distribution. The method then advances to step S16, in which an unsupervised classification algorithm is applied to the distribution to calculate a probability, or likelihood, that a voxel with a given intensity corresponds to a particular tissue type, such as the wall or the lumen. Hence, a likelihood of each tissue type can be allocated to each voxel in the region.

Any known technique can be used for the classification algorithm, which will estimate the mean, variance and weight of each of the two distributions in the two-class distribution in order to arrive at the probability for each intensity. For example, the k-means algorithm can be used, as described by J B McQueen in "Some methods for classification and analysis of multivariate observations" (*Proceedings of the Fifth Symposium on Math, Statistics, and Probability*, pages 281-297, University of California Press, 1967) and by J Marroquin and F Girosi in "Some extension of the k-means algorithm for image segmentation and pattern recognition" (*Al Memo* 1390, Massachusetts Institute of Technology, Cambridge, Mass., 1993). Also, the expectation-maximization (EM) algorithm could be used, as described by T K Moon in "The expectation-maximization algorithm" (*Signal Processing Magazine*, IEEE, vol. 13, pages 47-60, November 1996). The EM algorithm could be used in conjunction with the k-means algorithm.

Returning to FIG. 12, step S17 checks for any more regions. If there are regions for which no probability calculation has yet been performed, the method repeats steps S14, S15 and S16 until all regions have been processed. Alternatively, the calculations for each region may be performed simultaneously, so that there is no need for the iterative loop in FIG. 12.

In step S18, each of the voxels has tissue type or class probabilities assigned to it, according to the probabilities calculated in step S16. If there an overlap between the regions has been used, the voxels in the overlapping areas are assigned probabilities according to the relative weights of the kernels applied to the adjacent regions. This produces a smoothing effect between the regions.

Hence, the classification method of this embodiment divides a vessel into small segments before applying a weighting in an early stage of an unsupervised classification technique, to provide an improvement to existing unsupervised techniques. The division of the vessel into small segments has the effect of sharpening the two-class distribution of voxel intensities, which enables a better separation between the lumen and the wall distributions, so that tissue type probabilities can be determined more accurately.

Note that the embodiment can be implemented using any number of segments and any number of regions. Also, any shape of kernel can be used. For example, limiting cases include a single region with a flat kernel, in which the segments do not have any overlapping information, and a single segment (giving a single region) with a flat kernel. Results are likely to be enhanced by the use of large numbers of segments and regions, however.

While the classification embodiment has been described with reference to the example of a vessel comprising a lumen and a wall, it is expected that the method will be equally beneficial in determining probabilities for tissue types in other anatomical regions.

Also, the classification method may be applied to image data sets obtained by imaging regimes other than computed tomography, such as magnetic resonance imaging.

Once the voxels have been assigned probabilities, it is possible to segment voxels of a particular tissue type from the data set by using the probabilities. In the present example, the lumen voxels and/or the vessel wall voxels can be segmented. This is shown in step S19 of FIG. 12. The segmentation is optional, according to the medical analysis being conducted. The assigned probabilities could equally be used for other or additional applications.

As an example, segmentation of the lumen can be performed using a standard level-set approach. A technique for this is described by Yan Yang et al in "Knowledge based 3D segmentation and reconstruction of coronary arteries using CT images" (Engineering in Medicine and Biology Society, 2004, IEMBS '04 26th Annual International Conference of the IEEE, pages 1664-1666, 2004). Vessel tissue classification probabilities (such as those calculated according to the embodiment of FIG. 12) are used to weight a speed function driving a level-set, and a calcium threshold (such as that calculated according to the embodiment of FIG. 2) is used to prevent the inclusion of calcified plaque.

For segmentation of the vessel wall voxels from those of the surrounding tissue, several techniques are known. Some are active contours models, or "snakes", which seek to minimize some form of "energy" or "cost" function, for which various definitions exist. An example is given by D Vukadinovic et al in "Segmentation of the outer vessel wall of the common carotid artery in CTA" (*IEEE Medical Imaging*, vol. 29. No. 1, January 2010). This technique includes the steps of constructing 2D images perpendicular to the vessel centerline, segmenting the lumen, classifying and removing any calcification, classifying pixels as being within or outside the vessel, and finally, fitting an ellipsoid "contour" describing the vessel wall. The ellipsoid contour is fitted by minimizing an energy function that is the sum of random samples of the classification within the ellipse divided by the number of random samples.

This approach has a number of disadvantages. The classification does not distinguish between the lumen and the vessel wall, which reduces sensitivity to branching in the vessel. The tissue classification has spatial information encoded in it, which causes the classification to be dependent on the supervised training used to obtain it so that it may not handle regional variations such as patient ethnicity. The energy is sampled within the ellipsoid contour, which is an approximation that may reduce accuracy. Also, the use of 2D images produces a set of 2D contours that are fit sequentially from the start of the vessel to the end with constraints applied between the image slices. This prevents simultaneous evaluation of the contours, which reduces efficiency.

Embodiments of the present invention aim to address some of these disadvantages, with particular focus on the tissue classification and the energy function and minimization.

For the tissue classification, no attempt need be made to classify the tissue external to the vessel, i.e. the voxels lying outside the vessel wall. This "background" tissue typically has large variations and a non-uniform distribution, so is difficult to classify. Hence, any method that does not require such classification is advantageous.

Then, the vessel voxels can be classified as representing the vessel wall or the lumen. The classification will be in the form of probabilities, and may be obtained using the method of FIG. 12, with Gaussian distributions. However, any method may be used to construct suitable distributions and calculate the probabilities. A method such an that of FIG. 12, that does not use supervised learning, will give tissue classification results that are not directly correlated with spatial information, thereby avoiding possible bias in classification over different geographical regions arising from issues such as known differences in vessel size due to genetic variation.

Once the classified vessel voxels are obtained, they can be used as an input to a method for segmenting the vessel wall according to an embodiment of the invention.

Figure 15:
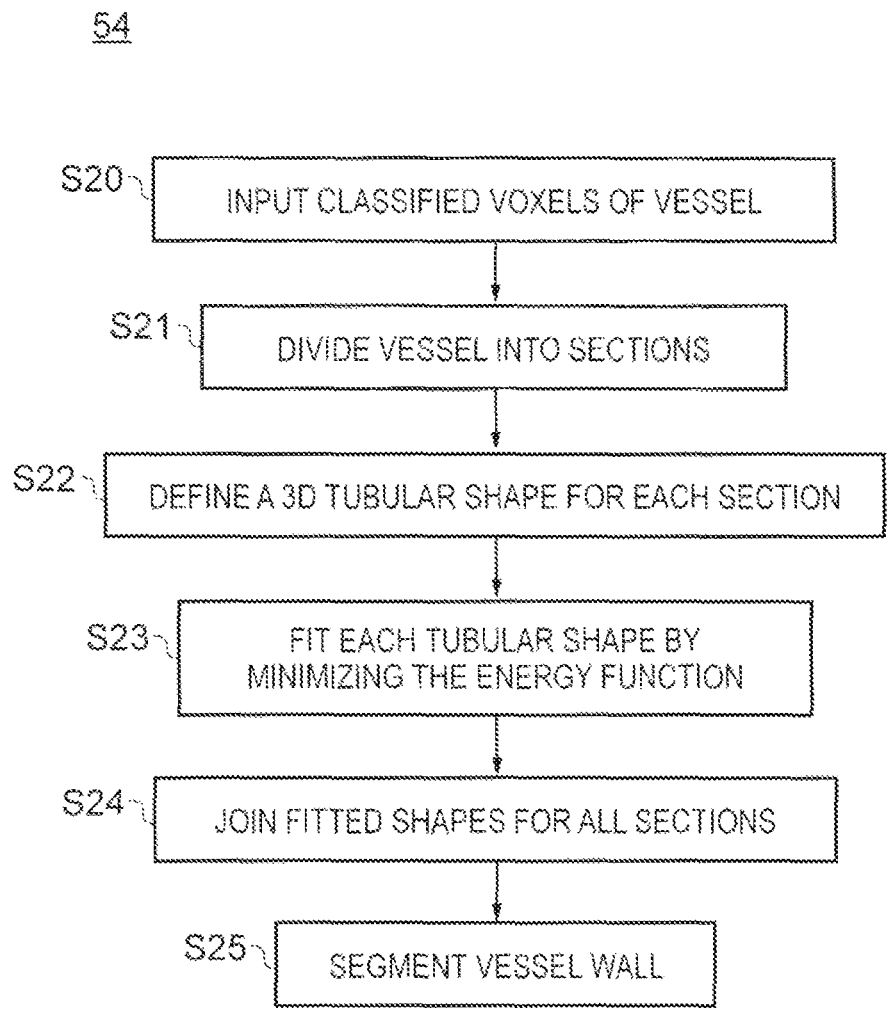
FIG. 15 shows a flow chart of a method for segmenting vessel wall voxels according to an embodiment of the invention.

FIG. 15 shows a flowchart of an embodiment of a method 54 for segmenting a vessel wall. Beginning at step S20, the classified vessel voxels are taken as an input. Voxels classified by alternative methods than that of method 52 in FIG. 12 may alternatively be used.

Moving to step S21, the vessel, as represented by the voxels, is divided into a plurality of sections along its length. The sections may or may not overlap.

In step S22, for each section a generally tubular geometrical shape is defined, the shape intended to roughly model the outer surface of the vessel wall. Any reasonable shape can be selected. For example, elliptical cylinders have been found to give good results. The elliptical cylinder may further be conical. Straight or conical circular cylinders might be used instead. The invention is not limited to any of these example 3D shapes, however. Other geometrical shapes that approximate the general tubular shape of the vessel wall may be used.

Whatever shape is chosen, the defined tubular geometrical shape is taken to represent a 3D energy or cost function, where the function is defined as:

$$\text{Energy} = A \int P(I) dv + B \oint \nabla I \cdot \hat{u} d\sigma / \oint d\sigma + C \oint (I_0 - I)^2 d\sigma / \oint d\sigma$$

where A, B and C are constants.

The first term represents a volume integral within the tubular shape of the probability classification of the voxels as vessel wall P(I), where I is the voxel intensity. Its value increases with increasing probability, and this part of the function tends to cause the bounds of the tubular shape to expand;

The second term is a surface integral on the tubular shape of the surface normal $\hat{u}$ component of the image intensity gradient dI. Its value increases if the gradient is normal to the surface. Also, this part of the function prefers boundaries with a larger gradient.

The third term is a surface integral on the tubular shape, of the deviation of the voxel intensity I from the average intensity $I_0$ on the surface, also known as the variance. This part of the function prefers a uniform intensity along the bounds of the tubular shape. Its inclusion in the energy function helps to remove branches from the vessel and prevents "bleeding" of the modeled vessel wall surface into neighboring tissue.

Returning to FIG. 15, in step S23 of the method, each tubular shape is "fitted" by minimizing the energy function.

The minimized energy function is taken as a model or representation of the vessel outer wall over the relevant section of the vessel. In this way, the tubular shape has been fitted to the vessel wall, in a series of adjacent sections which may or may not overlap. An advantage of this embodiment is that the sections can be fitted simultaneously, to give an output more quickly. However, the invention is not so limited, and the sections could be fitted one or more at a time, in sequence or not, as preferred.

Step S24 of the method takes the minimized energy functions, each representing a section of the vessel, and connects the sections to allow the fitted tubular shapes to be aligned or joined together. This may be done, for example, by applying one or more constraints between the fitted shapes. For example, conditions such as the bounds are continuous, or the first derivatives at the bounds are continuous may be applied as constraints. Alternatively, a simple smoothing function might be applied over the junctions between adjacent fitted shapes. This joining or connecting of the individual fitted shapes produces a single fitted tubular shape that models the outer surface of the vessel wall over its full extent.

In step S25, the fitted tubular shape, which defines the boundary between the outer surface of the vessel wall and the surrounding tissue, and hence demarcates vessel wall voxels from non-vessel wall voxels, is used to segment the voxels of the vessel wall from the remaining voxels.

Similarly to the calcium identification embodiment, the vessel wall and lumen classification embodiment and the vessel wall segmentation embodiment discussed with reference to the examples of FIGS. 12 and 15 are computer-implemented methods which may be performed using apparatus such as that shown in FIGS. 6-9.

Each of the methods for identifying calcification, classifying tissue and segmenting vessel walls can be used individually and separately, either as isolated procedures, or as stages in longer imaging processing techniques. However, as indicated throughout the description, the methods can be used together in any combination.

Figure 16:
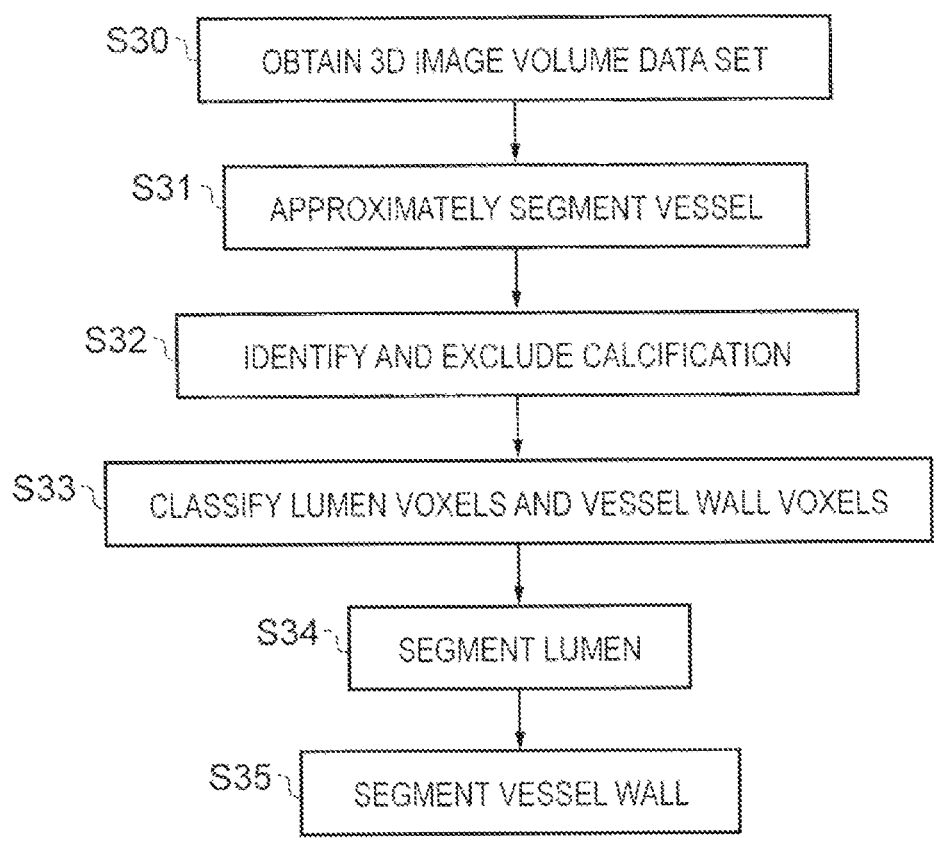
FIG. 16 shows a flow chart of a method for processing an image data set by identifying calcification, classifying lumen and vessel wall voxels, and segmenting vessel wall voxels according to a further embodiment of the invention.

FIG. 16 shows a flow diagram of an example method 56 that incorporates each of the above-described embodiments. As a first step S30, a 3D volume data set comprising voxels with intensity values is obtained, perhaps from a contrast-enhanced coronary CTA patient imaging procedure. One or more blood vessels or vessel networks are approximately segmented out from the data set as a whole.

Next, in step 32 any voxels representing calcification are identified and excluded from the data set, using the method 50 of FIG. 2.

After the removal of calcium, the method proceeds to step S33 in which the remaining voxels are classified as being either lumen or vessel wall, by applying the method 52 of FIG. 12. The lumen voxels are then segmented from the data, in step S34.

Finally, in step S35 the vessel wall voxels are segmented, using the method 54 of FIG. 15.

While certain embodiments have been described, these embodiments have been presented by way of example only, and are not intended to limit the scope of the inventions. Indeed, the novel methods, computers, computer program products and image acquisition devices described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed:

1. A computer system operable to identify calcification in a patient image data set showing one or more blood vessels, the computer system comprising:
a mass storage device for storing patient image data sets; and
a processor unit operable to execute machine-readable instructions to:
(a) obtain an image data set from the mass storage device, the image data set comprising voxels each having an intensity value;
(b) form the intensity values into a group of intensity values, the intensity values covering an intensity range;
(c) define a plurality of intensity thresholds with values spaced across the intensity range and including the end values of the intensity range;
(d) for each of the plurality of intensity thresholds:
(i) partition the group of intensity values into two subgroups according to the intensity threshold; and
(ii) calculate an information criterion as a function of the intensity threshold;
(e) generate an information criterion measure curve, being a plot of the calculated information criteria against intensity threshold;
(f) locate a maximum in the information criterion measure curve and set the corresponding intensity threshold to be a calcification threshold; and
(g) partition the group of intensity values into two subgroups using the calcification threshold, thereby identifying the voxels corresponding to the intensity values in the sub-group above the calcification threshold as representing calcification in the patient.

2. The computer system according to claim 1, wherein the information criterion is the Bayesian information criterion.

3. The computer system according to claim 1, wherein the information criterion is the Akaike information criterion.

4. The computer system according to claim 1, wherein the information criterion is the covariance information criterion.

5. The computer system according to claim 1, wherein the image data set is a contrast computed tomographic angiography image data set, so that lumen of the one or more blood vessels contain contrast-enhanced blood.

6. The computer system according to claim 1, wherein the image data set is a non-contrast computed tomographic angiography image data set, so that lumen of the one or more blood vessels contain non-contrast-enhanced blood.

7. The computer system according to claim 1, wherein step (a) comprises obtaining the image data set by segmenting voxels from a patient image data set to obtain an image data set including a blood vessel of interest.

8. The computer system according to claim 7, wherein the segmenting comprises removing all voxels with intensities below a predetermined threshold to leave voxels corresponding to calcification and lumen.

9. The computer system according to claim 1, wherein after step (g), the processor unit is further operable to output to a user an indication of those voxels identified as representing calcification in the patient.

10. The computer system according to claim 1, wherein after step (g), the processor unit is further operable to execute machine-readable instructions to:
(h) segment the voxels representing calcification from the image data set.

11. The computer system according to claim 10, wherein after step (h), the processor unit is further operable to execute machine-readable instructions to:
(i) divide the voxels of the image data set that correspond to the one or more blood vessels into one or more segments along the vessel length;
(j) group adjacent segments together to form one or more regions;

(k) for each region:
    (i) apply a kernel across the region to assign a weight to each segment in the region;
    (ii) apply the weights to the intensity values of the voxels in the region to obtain a set of weighted voxel values;
    (iii) assume a multiple-class statistical distribution of the weighted voxel values, the classes being voxels representing lumen and vessel wall components; and
    (iv) calculate a probability that each voxel represents each class using a classification algorithm operating on the multiple-class statistical distribution; and (l) output an assignment of probabilities of each class to each voxel according to the calculated probabilities.

12. The computer system according to claim 11, wherein in step (j) adjacent segments are grouped to form overlapping regions.

13. The computer system according to claim 11, wherein the kernel is a Gaussian kernel.

14. The computer system according to claim 11, wherein the multiple-class statistical distribution is a Gaussian distribution.

15. The computer system according to claim 11, wherein the classification algorithm is an unsupervised classification algorithm comprising one or both of the k-means algorithm and the expectation-maximization algorithm.

16. The computer system according to claim 11, wherein the processor unit is further operable to execute machine-readable instructions to use the assignment of probabilities of step (l) to segment the voxels representing the lumen or the vessel wall from the image data set.

17. The computer system according to claim 11, wherein after step (l), the processor unit is further operable to execute machine-readable instructions to:

(m) divide the voxels of the image data set that correspond to the one or more blood vessels into a plurality of sections along the vessel length;

(n) for each section:
    (i) define a tubular shape as a model of the outer surface of the vessel wall;
    (ii) set the tubular shape to be a three-dimensional energy function comprising a first term that is a volume integral within the tubular shape of class probabilities assigned to each voxel in claim 11, a second term that is a surface integral on the tubular shape of the surface normal component of the voxel intensity gradient, and a third term that is a surface integral on the tubular shape of the deviation of voxel intensity from the average voxel intensity on the surface; and
    (iii) fit each tubular shape by minimizing the energy function;

(o) join the sections to align the fitted tubular shapes into a total fitted tubular shape that models the outer surface of the vessel wall along the vessel length; and (p) segment the voxels of the vessel using the total fitted tubular shape to distinguish the voxels of the vessel from other voxels.

18. The computer system according to claim 17, wherein the three dimensional energy function is defined as $$\text{Energy} = A\int P(I)dv + B\oint \nabla I \cdot \hat{u} d\sigma / \oint d\sigma + C\oint (I_0 - I)^2 d\sigma / \oint d\sigma$$

where A, B and C are constants; the first term represents a volume integral within the tubular shape of the probability of the voxels being vessel wall P(I) and I is the voxel intensity; the second term is a surface integral on the tubular shape of the surface normal $\hat{u}$ component of the image intensity gradient $\nabla I$; and the third term is a surface integral on the tubular shape of the deviation of the voxel intensity I from the average intensity $I_0$ on the surface.

19. The computer system according to claim 17, wherein the defined tubular shape is an elliptical cylinder.

20. The computer system according to claim 17, wherein in step (o) the fitted tubular shapes are aligned by applying constraints between the sections.

21. The computer system according to claim 17, wherein in step (o) the fitted tubular shapes are aligned by applying a smoothing function between the sections.

22. An image acquisition device comprising a computer system according to claim 1.

23. An image acquisition device comprising a computer system according to claim 11.

24. An image acquisition device comprising a computer system according to claim 17.

25. A method of identifying calcification in a patient image data set showing one or more blood vessels, the method comprising:

(a) obtaining an image data set comprising voxels each having an intensity value;

(b) forming the intensity values into a group of intensity values, the intensity values covering an intensity range;

(c) defining a plurality of intensity thresholds with values spaced across the intensity range and including the end values of the intensity range;

(d) for each of the plurality of intensity thresholds:
    (i) partitioning the group of intensity values into two sub-groups according to the intensity threshold; and
    (ii) calculating an information criterion as a function of the intensity threshold;

(e) generating an information criterion measure curve, being a plot of the calculated information criteria against intensity threshold;

(f) locating a maximum in the information criterion measure curve and setting the corresponding intensity threshold to be a calcification threshold; and (g) partitioning the group of intensity values into two sub-groups using the calcification threshold, thereby identifying the voxels corresponding to the intensity values in the sub-group above the calcification threshold as representing calcification in the patient.

26. The method according to claim 25, wherein the information criterion is the Bayesian information criterion.

27. The method according to claim 25, wherein the information criterion is the Akaike information criterion.

28. The method according to claim 25, wherein the information criterion is the covariance information criterion.

29. The method according to claim 25, wherein the image data set is a contrast computed tomographic angiography image data set, so that lumen of the one or more blood vessels contain contrast-enhanced blood.

30. The method according to claim 25, wherein the image data set is a non-contrast computed tomographic angiography image data set, so that lumen of the one or more blood vessels contain non-contrast-enhanced blood.

31. The method according to claim 25, wherein obtaining the image data set comprises segmenting voxels from a patient image data set to obtain an image data set including a blood vessel of interest.

32. The method according to claim 31, wherein the segmenting comprises removing all voxels with intensities below a predetermined threshold to leave voxels corresponding to calcification and lumen.

33. The method according to claim 25 and further comprising, after step (g), outputting to a user an indication of those voxels identified as representing calcification in the patient.

34. The method according to claim 25 and further comprising, after step (g):
(h) segmenting the voxels representing calcification from the image data set.

35. The method according to claim 34, and further comprising, after step (h):
(i) dividing the voxels of the image data set that correspond to the one or more blood vessels into one or more segments along the vessel length;
(j) grouping adjacent segments together to form one or more regions;
(k) for each region:
  (i) applying a kernel across the region to assign a weight to each segment in the region;
  (ii) applying the weights to the intensity values of the voxels in the region to obtain a set of weighted voxel values;
  (iii) assuming a multiple-class statistical distribution of the weighted voxel values, the classes being voxels representing lumen and vessel wall components; and
  (iv) calculating a probability that each voxel represents each class using a classification algorithm operating on the multiple-class statistical distribution; and
(l) assigning probabilities of each class to each voxel according to the calculated probabilities.

36. The method according to claim 35, wherein in step (j) adjacent segments are grouped to form overlapping regions.

37. The method according to claim 35, wherein the kernel is a Gaussian kernel.

38. The method according to claim 35, wherein the multiple-class statistical distribution is a Gaussian distribution.

39. The method according to claim 35, wherein the classification algorithm is an unsupervised classification algorithm comprising one or both of the k-means algorithm and the expectation-maximization algorithm.

40. The method according to claim 35, and further comprising using the probabilities assigned in step (l) to segment the voxels representing the lumen or the vessel wall from the image data set.

41. The method according to claim 35, and further comprising, after step (l):
(m) dividing the voxels of the image data set that correspond to the one or more blood vessels into a plurality of sections along the vessel length;
(n) for each section:
  (i) defining a tubular shape as a model of the outer surface of the vessel wall;
  (ii) setting the tubular shape to be a three-dimensional energy function comprising a first term that is a volume integral within the tubular shape of probabilities of class assigned to each voxel in claim 37, a second term that is a surface integral on the tubular shape of the surface normal component of the voxel intensity gradient, and a third term that is a surface integral on the tubular shape of the deviation of voxel intensity from the average voxel intensity on the surface; and
  (iii) fitting each tubular shape by minimizing the energy function;
(o) joining the sections to align the fitted tubular shapes into a total fitted tubular shape that models the outer surface of the vessel wall along the vessel length; and
(p) segmenting the voxels of the vessel using the total fitted tubular shape to distinguish the voxels of the vessel from other voxels.

42. The method according to claim 41, wherein the three dimensional energy function is defined as $$\text{Energy} = A\int P(I)dv + B\oint \nabla I \cdot \hat{u} d\sigma / \oint d\sigma + C \oint (I_0 - I)^2 d\sigma / \oint d\sigma$$

where A, B and C are constants; the first term represents a volume integral within the tubular shape of the probability of the voxels being vessel wall $P(I)$ and $I$ is the voxel intensity; the second term is a surface integral on the tubular shape of the surface normal $\hat{u}$ component of the image intensity gradient $\nabla I$; and the third term is a surface integral on the tubular shape of the deviation of the voxel intensity $I$ from the average intensity $I_0$ on the surface.

43. The method according to claim 41, wherein the defined tubular shape is an elliptical cylinder.

44. The method according to claim 41, wherein in step (o) the fitted tubular shapes are aligned by applying constraints between the sections.

45. The method according to claim 41, wherein in step (o) the fitted tubular shapes are aligned by applying a smoothing function between the sections.

46. A non-transitory computer program product bearing machine-readable instructions for carrying out the method of claim 25.

47. A non-transitory computer program product bearing machine-readable instructions for carrying out the method of claim 35.

48. A non-transitory computer program product bearing machine-readable instructions for carrying out the method of claim 41.

* * * * *